(12) United States Patent
Gagliardi

(10) Patent No.: US 7,241,252 B1
(45) Date of Patent: Jul. 10, 2007

(54) FITNESS WEAR WITH HIDDEN BACK SUPPORT

(76) Inventor: Victor W. Gagliardi, 26 Loren Cir., Windsor, CT (US) 06095

( * ) Notice: Subject to any disclaimer, the term of this patent is extended or adjusted under 35 U.S.C. 154(b) by 26 days.

(21) Appl. No.: 11/010,690

(22) Filed: Dec. 13, 2004

(51) Int. Cl.
*A63B 21/02* (2006.01)
*A63B 23/00* (2006.01)
*A61F 5/00* (2006.01)
*A61L 15/00* (2006.01)
*F41H 1/02* (2006.01)
*F41H 1/04* (2006.01)
*A41B 9/00* (2006.01)

(52) U.S. Cl. ............... 482/124; 602/19; 602/5; 602/23; 602/75; 2/2.5; 2/400; 482/148

(58) Field of Classification Search .......... 482/124; 602/19, 23, 75–77; D02/731
See application file for complete search history.

(56) References Cited

U.S. PATENT DOCUMENTS

| | | | | |
|---|---|---|---|---|
| 3,771,171 A | * | 11/1973 | Mitchell ................. | 2/2.5 |
| 4,068,315 A | * | 1/1978 | Rainville ................. | 2/114 |
| 4,175,553 A | * | 11/1979 | Rosenberg ............... | 602/19 |
| 4,475,543 A | * | 10/1984 | Brooks et al. ............ | 602/19 |
| 5,046,488 A | * | 9/1991 | Schiek, Sr. .............. | 602/19 |
| 5,267,928 A | * | 12/1993 | Barile et al. ............. | 482/124 |
| 5,484,395 A | * | 1/1996 | DeRoche ................. | 602/19 |
| 5,536,246 A | * | 7/1996 | Saunders ................. | 602/19 |
| 5,651,763 A | * | 7/1997 | Gates ..................... | 602/19 |
| 5,728,055 A | * | 3/1998 | Sebastian ................ | 602/19 |
| 5,784,723 A | * | 7/1998 | Noble et al. ............. | 2/400 |
| 5,984,885 A | * | 11/1999 | Gaylord et al. .......... | 602/19 |
| 6,068,606 A | * | 5/2000 | Castel et al. ............ | 602/19 |

OTHER PUBLICATIONS

"Back Brace Belt: A Lower Back Pain Solution", Mar. 24, 2004, Ultimate Water Massage, p. 2.*

* cited by examiner

*Primary Examiner*—Stephen R. Crow
*Assistant Examiner*—Arun Chhabra
(74) *Attorney, Agent, or Firm*—Alix, Yale & Ristas, LLP

(57) ABSTRACT

A tapered elastic back support is situated in a fabric tube formed at the top edge of a variety of shorts and pants suitable for use during athletics, exercise or rehabilitative therapy. Unlike traditional back braces, the portion of the back support encircling the front of the wearer's abdomen is tapered to pass well beneath the wearer's navel, permitting low cut garment designs that expose significant portions of the wearer's abdomen. The rear portion of the back support increases in height to cover at least the lower three vertebrae (L5–L3). The front portion of the back support allows the wearer to tighten the appliance such that a continuous elastic stabilizing pressure is exerted across the lower back. Branched drawstring portions or tapered belt portions are secured to the elastic back support material and extend through the fabric tube at the front of the garment.

6 Claims, 5 Drawing Sheets

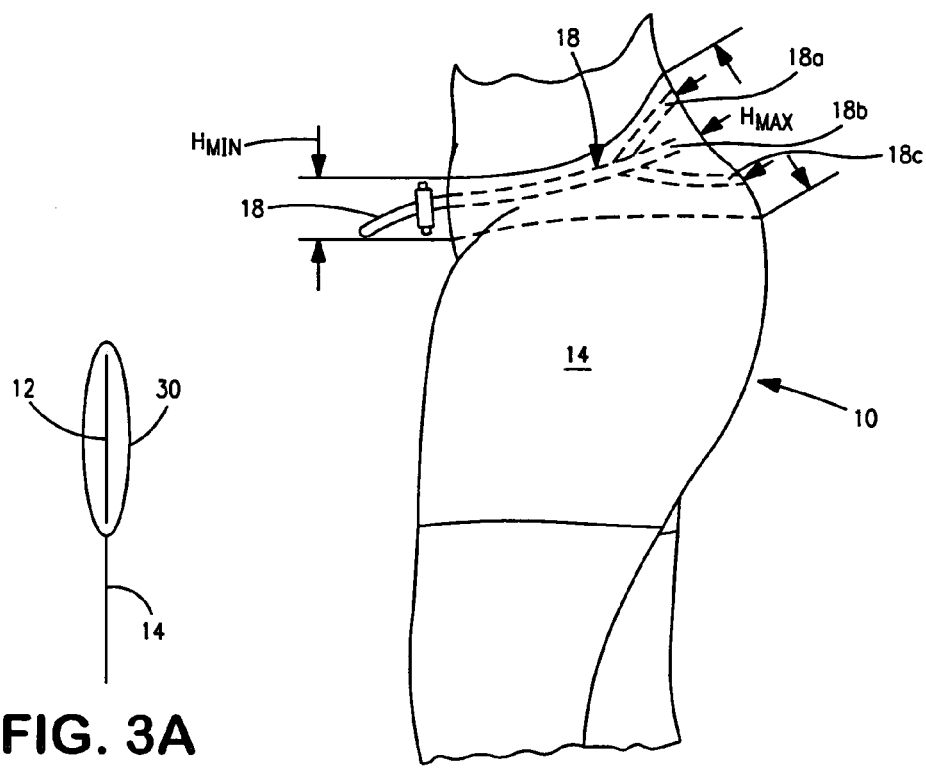
FIG. 3A
FIG. 3
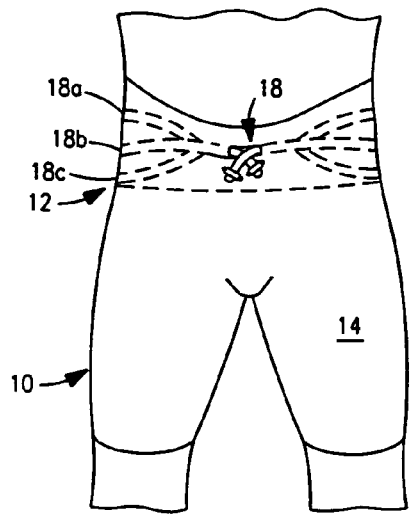
FIG. 4
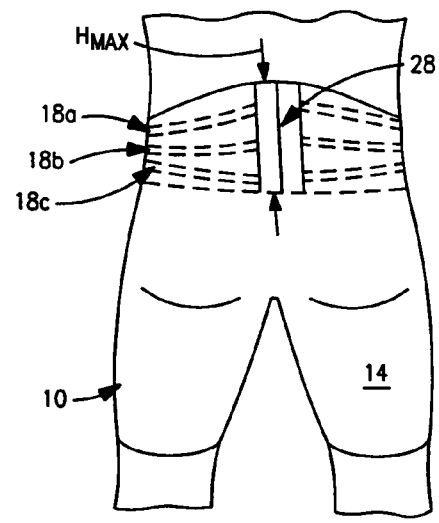
FIG. 5

FITNESS WEAR WITH HIDDEN BACK SUPPORT

BACKGROUND OF THE INVENTION

1. Field of the Invention

The invention relates generally to fitness wear, and more specifically to fitness wear including a concealed lower back support that does not detract from the appearance of the fitness wear.

2. Description of the Related Art

Many people suffer from lower back disorders resulting from job-related injuries, automobile accidents, age, or athletic injuries. Commonly, rehabilitation for lower back disorders involves prescribed physical therapy in combination with an exercise program. It is well established that a continuing regimen of regular physical exercise helps to control the symptoms of the disorder. Exercises or activities that stretch and/or strengthen the muscles of the abdomen are particularly effective in this regard.

For those suffering from lower back disorders, it is advisable to stabilize the lower back during physical activity, therapy or exercise to prevent aggravation or reinjury to the lower back. Appliances for stabilizing the lower back, typically referred to as a "back brace", are frequently employed to stabilize the lower back of those suffering from lower back disorders during work and/or exercise. Such back braces can be rigid or flexible. The most common back braces are wide belt-like garments constructed to encircle the user's abdomen from just above the hipbones to above the navel, stabilizing the five lumbar vertebrae. While such back braces are effective at stabilizing the lumbar vertebrae, they are typically entirely functional and unsightly garments from a fashion perspective. Further, the wide belt encircles the abdominal portion of the wearer's torso making exercises involving the abdominal muscles difficult or uncomfortable. It is known for wearers of back braces to remove the back brace entirely during abdominal exercises and thus risk re-injury during such exercises. Another reason why such prior art back braces are not worn is that they are singularly unattractive. Many fitness garments, particularly those designed for women, are configured to expose the woman's midriff. Wearing a traditional back brace in the form of a wide belt completely encircling and covering the abdomen is unappealing to many men and women from a fashion perspective.

SUMMARY OF THE INVENTION

Fitness wear with hidden back support according to aspects of the invention integrates a tapered elastic back support within a variety of shorts and pants suitable for use during athletics, exercise or rehabilitative therapy. Unlike traditional back braces, the portion of the back support encircling the front of the wearer's abdomen is tapered to pass well beneath the wearer's navel, permitting back support in fitness wear exposing significant portions of the wearer's abdomen. The rear portion of the back support increases in height to cover at least the lower three vertebrae (L3–L5). Also unlike traditional back braces, the back support is concealed within the fitness wear garments such as shorts, sweat pants, Capri pants or jogging suits. The back support is covered by at least one layer of fabric so that the fitness wear does not appear to include a back support. The front portion of the fitness wear includes means for tightening the back support around the waist of the user such that a continuous elastic stabilizing pressure is exerted across the lower back of the user. A draw string or strap with a buckle or hook and loop attachment extends through the fabric at the front of the fitness wear to permit the user to adjustably tighten the back support. The back support is shaped such that it naturally follows the curve of the user's lower back and remains substantially located over the user's lower back during use.

BRIEF DESCRIPTION OF THE FIGURES

FIG. 3 is a side view, partly in phantom, of a first embodiment of an article of fitness wear according to aspects of the present invention;

FIG. 4 is a front view, partly in phantom, of the article of fitness wear shown in FIG. 1;

FIG. 5 is a rear view of the an article of fitness wear shown in FIG. 1;

DETAILED DESCRIPTION OF THE PREFERRED EMBODIMENTS

Figure 1:
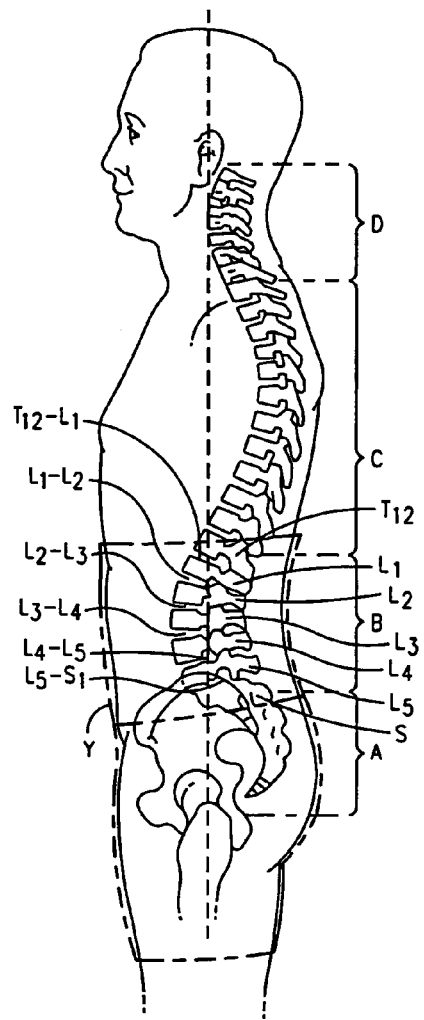
FIG. 1 is a diagrammatic side view of a human body illustrating the four defined physiological curve regions of the spine.
Figure 2:
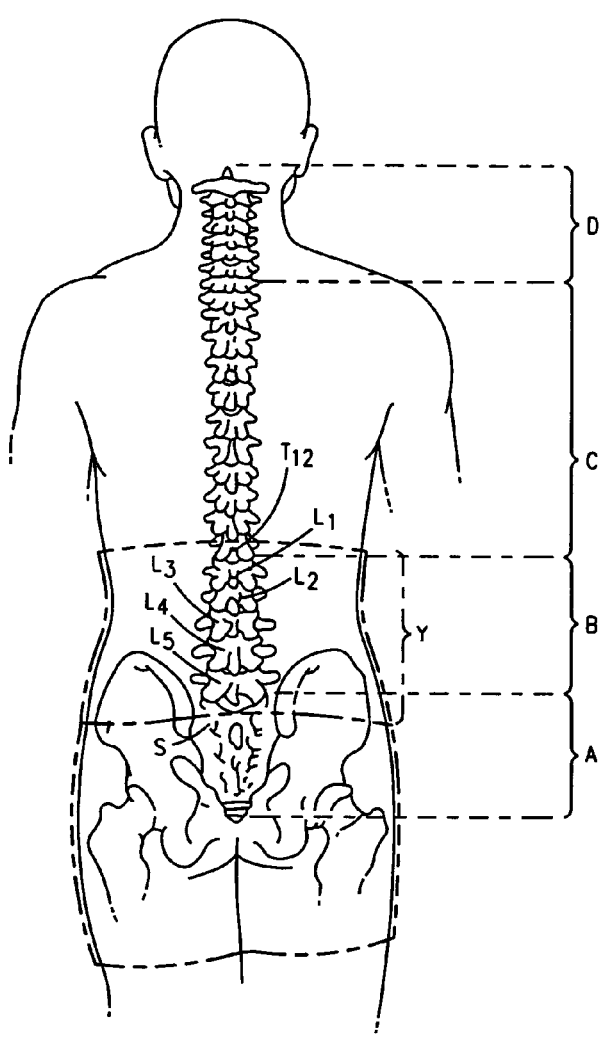
FIG. 2 is a diagrammatic representation of the human body of FIG. 1, illustrated from a back or posterior position.
Figure 6:
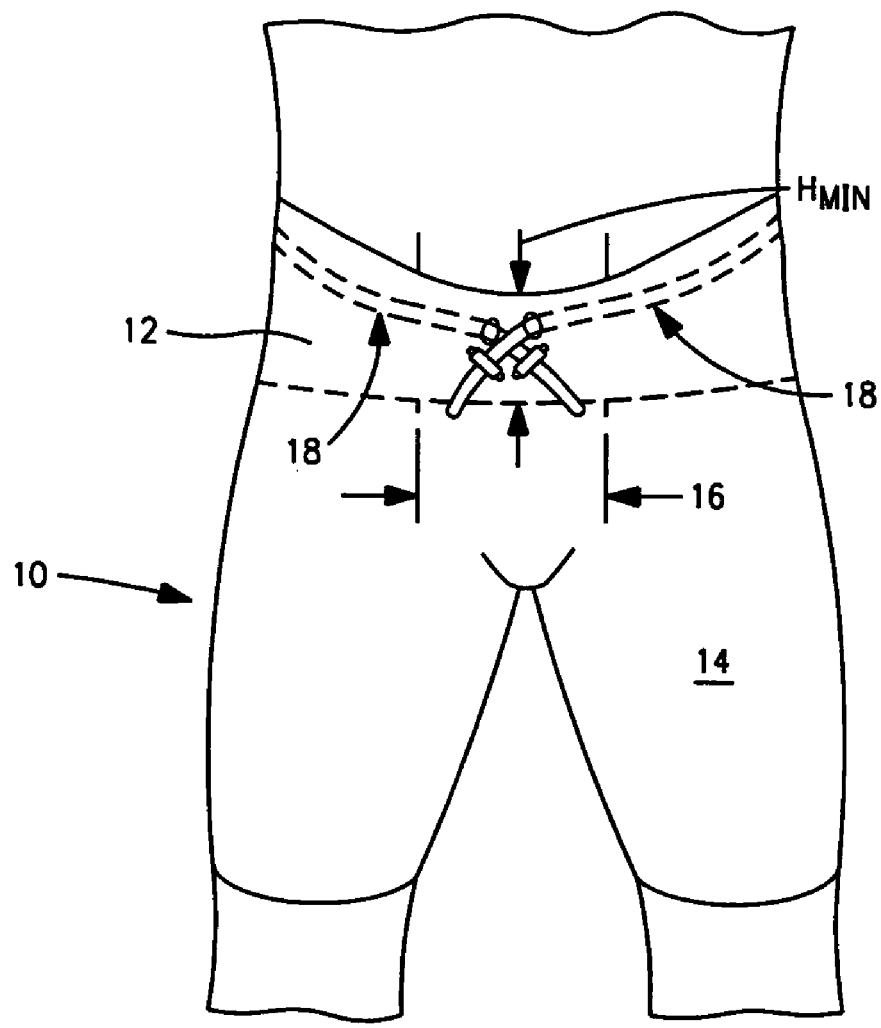
FIG. 6 is a front view of an article of fitness wear according to aspects of the present invention, showing an alternative draw string configuration.

Preferred embodiments of fitness wear for rehabilitation will now be described with reference to FIGS. 1–8. FIGS. 1 and 2 illustrate the primary skeletal features of the human body that relate to the present invention. The human spinal column extends from the sacrum S at letter A to the cervical vertebrae at letter D. Letter B illustrates that portion of the spinal column occupied by the five lumbar vertebrae L1 through L5. Letter C illustrates that portion of the spinal column made up by the twelve thoracic vertebrae with thoracic vertebrae T12 forming a joint with the upper most lumbar vertebrae L1 at T12-L1. Other inter-lumbar joints are shown between the respective 5 lumbar vertebrae and the lower most vertebra L5 and the sacrum S1 at L5-S1. The girdle-like encirclement Y shown at FIGS. 1 and 2 illustrates a constant width belt-like garment typically employed in the prior art back brace. The girdle-like encirclement Y extends from the sacrum S upwardly to approximately the lower most thoracic vertebrae T12. Such constant width back brace belts can be somewhat narrower in width, configured to extend between the sacrum S and the middle lumbar vertebra L3. The constant width of the belt-like back brace was believed necessary to stabilize the joints between the lower vertebrae.

FIGS. 3 through 6 are views of a first embodiment 10 of an article of fitness wear incorporating a hidden back support 12 according to the present invention. FIG. 3 is a side view of a short-type garment illustrating a tapered back support 12 integrated within the garment 14. The back support 12 tapers from a maximum height $H_{MAX}$ extending around the back of the wearer to a minimum height $H_{MIN}$ directly beneath the navel of the user. $H_{MAX}$ may be approximately 8 to 14 inches, depending on the size of the garment and the style of the back support, while the corresponding $H_{MIN}$ may be approximately 2 to 6 inches. The lateral extent 16 of the region of minimum height $H_{MIN}$ may vary from a few inches immediately beneath the user's navel to a larger portion across the front of the user's abdomen. The back support 12 illustrated in FIG. 1 is tightened around the waist of the user by a drawstring 18. The drawstring 18 branches into an upper branch 18a, a middle branch 18b and a lower branch 18c. The three branches of the drawstring are joined to the drawstring 18 that extends through the fabric of the shorts at the front of the garment. The branched drawstring allows the single drawstring 18 to tighten the back support across its height $H_{MAX}$.

The body of the back support 12 is constructed from one or more bands of elastic material, stitched together if necessary. The elastic material is entirely concealed within a fabric tube 30 formed at the top of the shorts 14 (see FIG. 3A). The back support 12 moves freely within the fabric tube 30. The branched drawstring 18, 18a, 18b, 18c ensures that elastic pressure is applied to the user's lower back across the entire height $H_{MAX}$ of the rear portion of the back support 12.

The height $H_{MAX}$ of the rear portion of the back support 12a is at least twice the height $H_{MIN}$ of the front most portion of the back support, i.e., that portion of the support immediately beneath the user's navel. The back support 12 is tapered from $H_{MAX}$ in the center of the user's back to $H_{MIN}$ at the center of the user's abdomen. FIGS. 3–5 illustrate the angled relationship between upper and lower branches of the drawstring 18a, 18c. The angled drawstring branches are fixed to upper and lower portions of the of elastic back support material at the tapered side of the back support 12. The tightening means is configured so that it is attached to the elastic material of the back support adjacent a top edge, the middle and the bottom edge of the elastic material. This configuration ensures that stabilizing elastic pressure is substantially evenly applied across the full height $H_{MAX}$ of the rear portion of the back support 12. This substantially even pressure provides useful stabilization of the user's lower back without requiring the bulky and obtrusive configuration of the prior art back brace. In particular, the tapered configuration of the back support elastic material and the tightening means eliminates the wide front portion of the traditional back support, which can be uncomfortable and unsightly. Those in need of back support are more likely to use a support that is attractive and comfortable.

Figure 7:
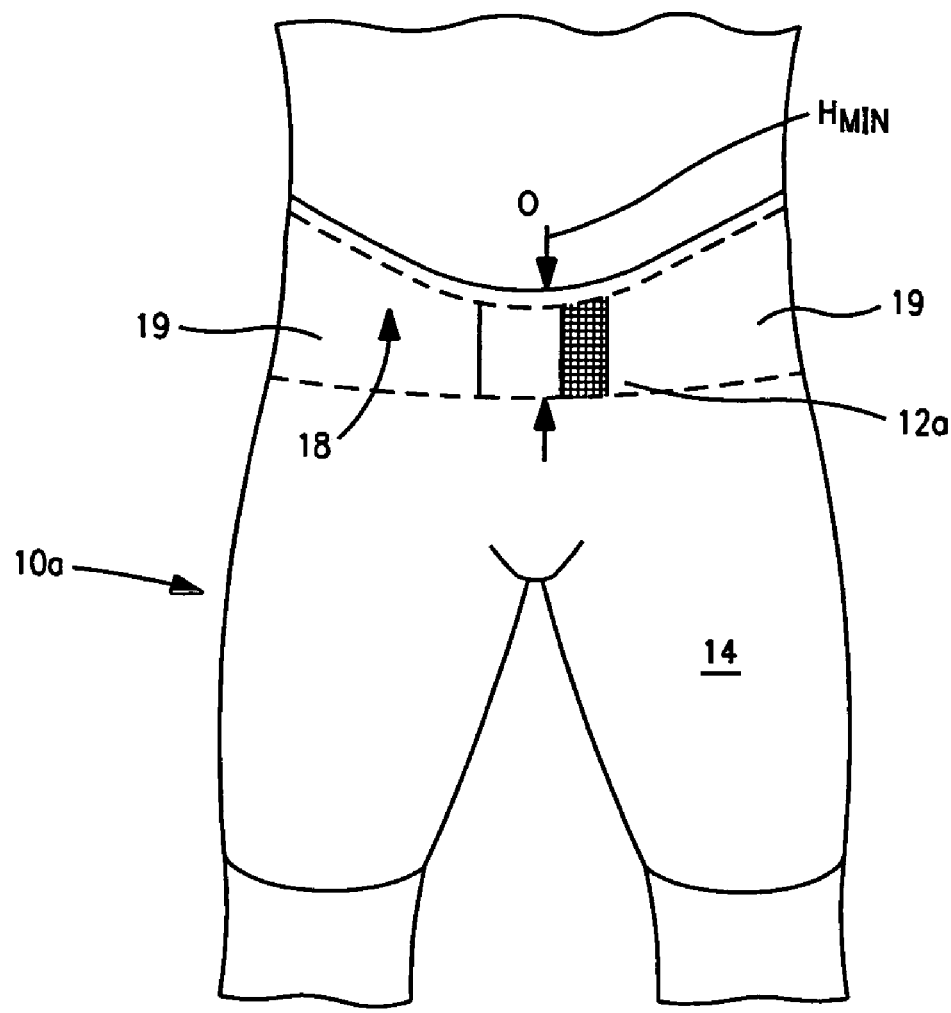
FIG. 7 is a front view, partly in phantom of an alternative embodiment of an article of fitness wear incorporating a belt with a hook and loop attachment.

FIG. 7 illustrates an alternative embodiment of a short-type fitness garment 14 equipped with a hidden back support 12a according to aspects of the present invention. The back support 12a of FIG. 7 includes two tapered belt portions 19 attached to the elastic material of the back support 12a and extending through the material of the fitness garment to permit tightening of the back support by the user. The only portion of the back support visible is the ends of the belt which include velcro 26 for securing the belt portions 19 to each other at the selected tension. The back support 12a is free to move inside a fabric loop at the top of the shorts in a manner similar to that of the embodiment shown in FIGS. 3–5. The tapered configuration of the belt portions 19 applies tension over most of the height $H_{MAX}$ of the rear portion of the back support.

FIG. 5 is a rear view of the shorts 14 and back support 12 of FIG. 1. FIG. 5 illustrates three vertical stays 28 sown to the elastic fabric of the back support. These stays 28 help ensure that the back support remains flat against the user's lower back and does not bunch up with the branches of the drawstring 18a, 18b, 18c collapsing together. This stiffening of the rear portion of the back support also functions to provide added support to the user's lower spinal column. The stays 28 may be flexible or stiff and formed to conform to the curve of the wearer's lower back as shown in FIG. 1 at B.

Figure 8:
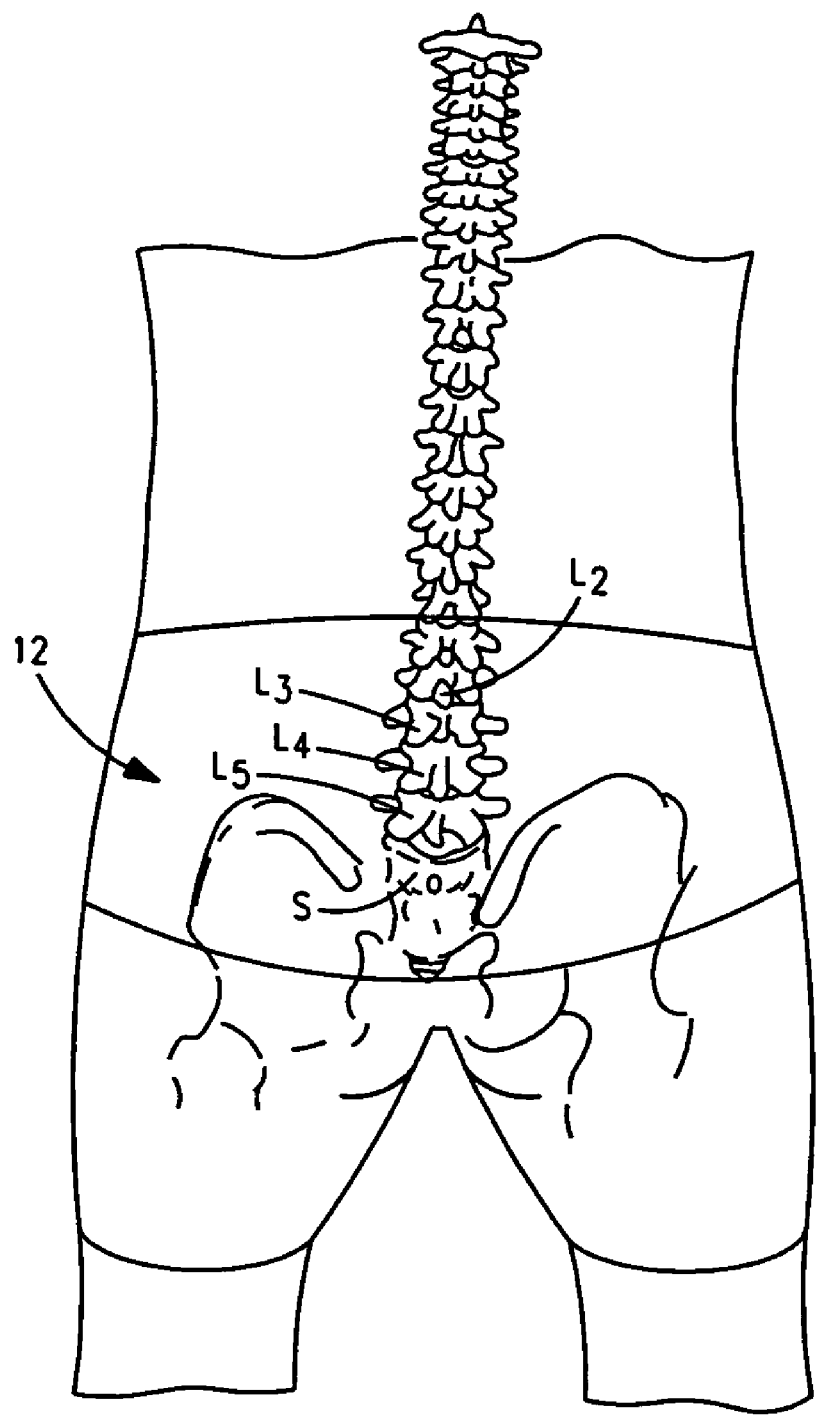
FIG. 8 is a posterior view of a human female pelvis and lower torso with the main skeletal features shown in phantom and the rear portion of a back support according to aspects of the present invention superimposed thereon.

FIG. 8 illustrates the lower torso and pelvic region of a user and superimposes the rear portion of an exemplary back support 12 over the principal skeletal features. Preferred embodiments of the back support 12 have a vertical height $H_{MAX}$ sufficient to extend from the sacrum S upwardly to cover at least the lower three lumbar vertebrae L5, L4, L3. The illustrated embodiments extend upwardly to also cover lumbar vertebra L2. In the back supports 12, 12a of the present invention, the vertical height $H_{MIN}$ of the front of the appliance will be approximately one-half the vertical height $H_{MAX}$ of the rear portion shown in FIGS. 3 and 6. This decreased vertical height $H_{MIN}$ improves the aesthetic appearance (fashion appeal) of a garment equipped with the appliance by permitting a low cut front and also significantly improves the comfort of the appliance to the wearer. Comfort is particularly important during exercise requiring forward bending of the torso relative to the legs.

It should be noted that the garments illustrated in the context of the present invention are not "compression-type" garments and will typically be knit-type garments. Knit garments are primarily elastic in only one direction and substantially inelastic in a direction perpendicular to their direction of primary elasticity. Thus, it should be noted that the garment itself will not serve to locate the back support relative to the user's body. The back support 12 is held in position primarily by the shape of the appliance. As best shown in FIGS. 3 and 5 the appliance has a shape which naturally seats against the concave curvature of the lower back. When drawn tightly around the user's waist, the back support 12, 12a seats itself and the garment hangs from the back support. Thus the position of the fitness garment 14 is determined by the position of the back support 12, 12a and not the reverse.

While preferred embodiments of the foregoing invention have been set forth for purposes of illustration, the foregoing description should not be deemed a limitation of the invention herein. Accordingly, various modifications, adaptations and alternatives may occur to one skilled in the art without departing from the spirit and the scope of the present invention.

I claim:

1. An article of fitness wear comprising:
   a garment portion configured to completely surround and cover a pelvic region and thighs of a wearer from the back to the front of the wearer, said garment portion comprising material having elasticity in one of a warp or a weft direction of the material, said material formed into a tube surrounding an upper edge of said garment portion; and
   a back support within said tube, said back support comprising:
      a tapered body including one or more bands of elastic material connected to extend around the wearer, said body having a rear portion with a maximum height $H_{MAX}$ extending between the sacrum and approximately lumbar vertebra L3 and tapering from the lower back, around the wearer to a front portion below the navel with a minimum height $H_{MIN}$, said maximum height $H_{MAX}$ being at least approximately twice said minimum height $H_{MIN}$, said body having an outside surface and an inside surface, wherein said body rear portion comprises a plurality of stays extending between an upper and lower edge of said rear portion; and means for tightening said body around the wearer, said means for tightening comprising two draw strings, each draw string having at least an upper branch and a lower branch, said upper and lower branches of each draw string being secured to the rear portion of said body against said plurality of stays at spaced apart locations of said outside surface, whereby each drawstring portion wraps around the lower back of the wearer and meets at each side of the wearer to form a central drawstring portion wherein each central drawstring portion includes a free end opposite said upper and lower branches, said free end extending towards the front and through the material of said tube so said free ends are exposed outside said tube, wherein said upper branch is secured at the sacrum and said lower branch is secured at the L3 lumbar vertebra against the lower back of the wearer so that pressure is applied to the lower back of the wearer to stabilize the lower three lumbar vertebrae L5–L3 during exercise by tying the central drawstring portions together.

2. The article of fitness wear of claim 1, wherein said body has an outside surface and an inside surface, said means for tightening comprises two tapered belt portions secured to the outside surface of said body rear portion at laterally spaced apart locations, each said tapered belt portion extending to hook and loop fasteners attached to overlapping end portions of said belt portions.

3. The article of fitness wear of claim 2, wherein said end portions extend through the fabric of said tube so said end portions are exposed outside the tube.

4. An article of fitness wear comprising:

a garment portion configured to completely surround and cover a pelvic region and thighs of a wearer from the back to the front of the wearer, said garment portion comprising material having elasticity in one of a warp or a weft direction of the material, said material formed into a tube surrounding an upper-edge of said garment portion; and a back support within said tube, said back support comprising:

a tapered body including one or more bands of elastic material connected to extend around the wearer, said body having a rear portion with a maximum height $H_{MAX}$ extending between the sacrum and approximately lumbar vertebra L3 and tapering from the lower back and around the wearer to a front portion below the navel with a minimum height $H_{MIN}$, said maximum height $H_{MAX}$ being at least approximately twice said minimum height $H_{MIN}$ said body having an outside surface and an inside surface a plurality of stays in said body rear portion and said plurality of stays extending between an upper and lower edge of said rear portion at spaced apart locations of said outside surface;

two tapered belt portions along the outside surface of said body and extending from the rear of said body and wrapping around the wearer to the front of said body and extending through laterally spaced openings in said tube of material, each of said tapered belt portions including means for adjustable connection to the other of said tapered belt portions, said connection being made outside said tube of material and in front of the wearer, wherein said support is free to move inside said tube and said tapered belt portions apply tension to said plurality of stays along a majority of the height $H_{MAX}$ of the rear portion of the back support during exercise as said means for adjustable connection are tightened or secured together.

5. The article of fitness wear of claim 4, wherein said means for adjustable connection comprises hook and loop fasteners.

6. The article of fitness wear of claim 4, wherein said means for adjustable connection comprises a belt and buckle.

* * * * *